(12) United States Patent
Tao et al.

(10) Patent No.: US 6,569,136 B1
(45) Date of Patent: May 27, 2003

(54) CLOTHLIKE, BREATHABLE BACKSHEET WITH MULTICOLORED GRAPHICS FOR DISPOSABLE ABSORBENT ARTICLE

(75) Inventors: Jie Tao, Ashiya (JP); Ebrahim Rezai, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/700,560

(22) PCT Filed: May 28, 1998

(86) PCT No.: PCT/US98/10853

§ 371 (c)(1),
(2), (4) Date: Nov. 16, 2000

(87) PCT Pub. No.: WO99/60973

PCT Pub. Date: Dec. 2, 1999

(51) Int. Cl.$^7$ .................................. A61F 13/15
(52) U.S. Cl. ............... 604/385.01; 604/379; 604/378; 604/390; 442/293; 428/138; 156/85
(58) Field of Search ................ 604/379, 378, 604/385.01, 370

(56) References Cited

U.S. PATENT DOCUMENTS

| | | | | |
|---|---|---|---|---|
| 5,034,078 A | * | 7/1991 | Hodgson et al. ............ 156/163 |
| 5,133,707 A | | 7/1992 | Rogers et al. ............... 604/389 |
| 5,458,590 A | * | 10/1995 | Schleinz et al. ............ 101/483 |
| 5,733,628 A | * | 3/1998 | Pelkie ........................ 428/132 |
| 5,897,541 A | * | 4/1999 | Uitenbroek et al. ......... 604/358 |

FOREIGN PATENT DOCUMENTS

EP   743052   * 12/1992   ........... A61F/13/15

* cited by examiner

Primary Examiner—John J. Calvert
Assistant Examiner—Angela T Grayson
(74) Attorney, Agent, or Firm—Jeffrey R. Moore; Jay A. Krebs; Ken K. Patel

(57) ABSTRACT

Disclosed is a disposable absorbent article comprising a topsheet, a backsheet and an absorbent layer between the topsheet and the backsheet, wherein the backsheet is comprised of a microporous polymer film printed with multi-colored graphics and a nonwoven material laminated to the film, wherein the film has a "b" value between about 0.0 and about 0.5 and exhibits less than about 4.0% thermal shrinkage at about 50° C. and about 50% relative humidity for one week.

7 Claims, 9 Drawing Sheets

CLOTHLIKE, BREATHABLE BACKSHEET WITH MULTICOLORED GRAPHICS FOR DISPOSABLE ABSORBENT ARTICLE

FIELD

The present invention relates to disposable absorbent articles such as disposable diapers and, more particularly to clothlike, breathable backsheets printed with multicolored graphics for use with such disposable absorbent articles.

BACKGROUND

Infants and other incontinent individuals wear disposable absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known in the art.

In the manufacture of disposable absorbent articles, such as diapers, microporous polymer films have generally been incorporated into the structure of the article as a part of the layers that are positioned away from the wearer's body during use (often called "the backsheet"). The backsheet provides a liquid impervious barrier so that exudates absorbed and contained in the absorbent core of the article are prevented from leaking, and particularly so that urine stains outside the diaper are prevented.

Some disposable diapers are provided with backsheets that provide the appearance of cloth and a cloth-like feel on the outside of the garment such that wearers and care-givers perceive a garment-like comfort. A typical structure of such a cloth-like backsheet comprises a nonwoven web joined to the outer-facing surface of a microporous thin plastic film to form a laminate.

For disposable absorbent articles, especially disposable diapers, it is also desirable to provide graphic designs on the articles to enhance their appearance and their consumer appeal. In previously known articles, the nonwoven layers have typically been printed with such graphic designs. This is because the printing process for nonwoven materials is typically easy to control, because the surfaces of such materials tend to provide stronger mechanical properties that make them more amenable to printing. However, high resolution, multi-colored graphics, which are consumer-preferred, usually cannot be printed on such materials. Thus the quality of the graphics that can be printed upon nonwoven materials is typically much lower than that which can be achieved by printing upon microporous films.

Microporous polymer films provide excellent surface characteristics that make them suitable for the printing of high resolution graphics. However, the existing microporous polymer films, see, e.g., Japanese Laid-Open Patent App. (Kokai) No. 9-25372, may not be mechanically stable enough to support the printing of the high resolution, multi-colored graphics that are consumer-preferred. This is due in part to their thermal instability, which has generally made it difficult to exploit their ability to support the application of high resolution multi-color graphics.

It has also been found that a high degree of whiteness, i.e., the visual appearance of the white color of the article as seen by the consumer, is very important to the consumer. Consumers tend not to accept articles that incorporate films having a yellowish or off-white shade. In addition, breathability, the ability of the article to allow water vapor to escape, is important for wearer comfort and for consumer skincare acceptance. A lack of breathability may result in a hot, stuffy, skin-unfriendly product for the wearer.

Based on the foregoing, there is a need for disposable absorbent articles comprising a cloth-like breathable backsheet having a film layer printed With multi-colored graphics. None of the existing absorbent articles provide all of the advantages and benefits of the present invention.

SUMMARY

The present invention is directed to a disposable absorbent article comprising a topsheet, a backsheet and an absorbent layer between the topsheet and the backsheet, wherein the backsheet is comprised of a microporous polymer film printed with multicolored graphics and a nonwoven material laminated to the film, wherein the film has a "b" value between about 0.0 and about 0.5 and exhibits less than about 4.0% thermal shrinkage at about 50° C. and about 50% relative humidity for one week.

These and other features, aspects, and advantages of the invention will become evident to those skilled in the art from a reading of the present disclosure.

BRIEF DESCRIPTION OF THE DRAWINGS

While the specification concludes with claims particularly pointing out and distinctly claiming the invention, it is believed that the present invention will be better understood from the following description of preferred embodiments taken in conjunction with the accompanying drawings in which:

DETAILED DESCRIPTION

All references cited herein are incorporated herein by reference in their entireties. Citation of any reference is not an admission regarding any determination as to its availability as prior art to the claimed invention.

All percentages herein are by weight of compositions unless specifically stated otherwise. All ratios are weight ratios unless specifically stated otherwise. As used herein, the term "comprising" means that other steps and other ingredients which do not affect the end result can be added. This term encompasses the terms "consisting of" and "consisting essentially of."

The microporous polymer films that are preferred for use in the disposable absorbent articles of the present invention are formed from a mixture of a polyolefin, usually supplied as a resin, and calcium carbonate ($CaCO_3$) particles. Exemplary polyolefins preferred for use herein include polyethylene and polypropylene. Alternatively, other thermoplastic polymers may be used for the films of the present invention.

The $CaCO_3$ is used to provide microporosity, as described more fully below. However, it may tend to impart a slight yellow shade to the film. It is believed that any such yellow shade is highly unacceptable to consumers, who tend to prefer a bright, intense white appearance. A bright white appearance can be achieved by selecting a grade of $CaCO_3$ that has a very white color. A bright white appearance can also be achieved by adding a small amount of titanium dioxide ($TiO_2$) to the polyolefin and $CaCO_3$ during the mixing stage of the film formation process, if the grade of $CaCO_3$ used is not white enough to provide the finished film with the desired whiteness. In such a case, the addition of the $TiO_2$ counteracts the yellowing effect of the $CaCO_3$.

$TiO_2$ is generally whiter than $CaCO_3$, but it is also generally more expensive and more difficult to blend during extrusion. If $TiO_2$ is added, preferably it should be added in an amount less than about 5 wt %, since amounts greater than about 5 wt % may be difficult to process.

Figure 1:
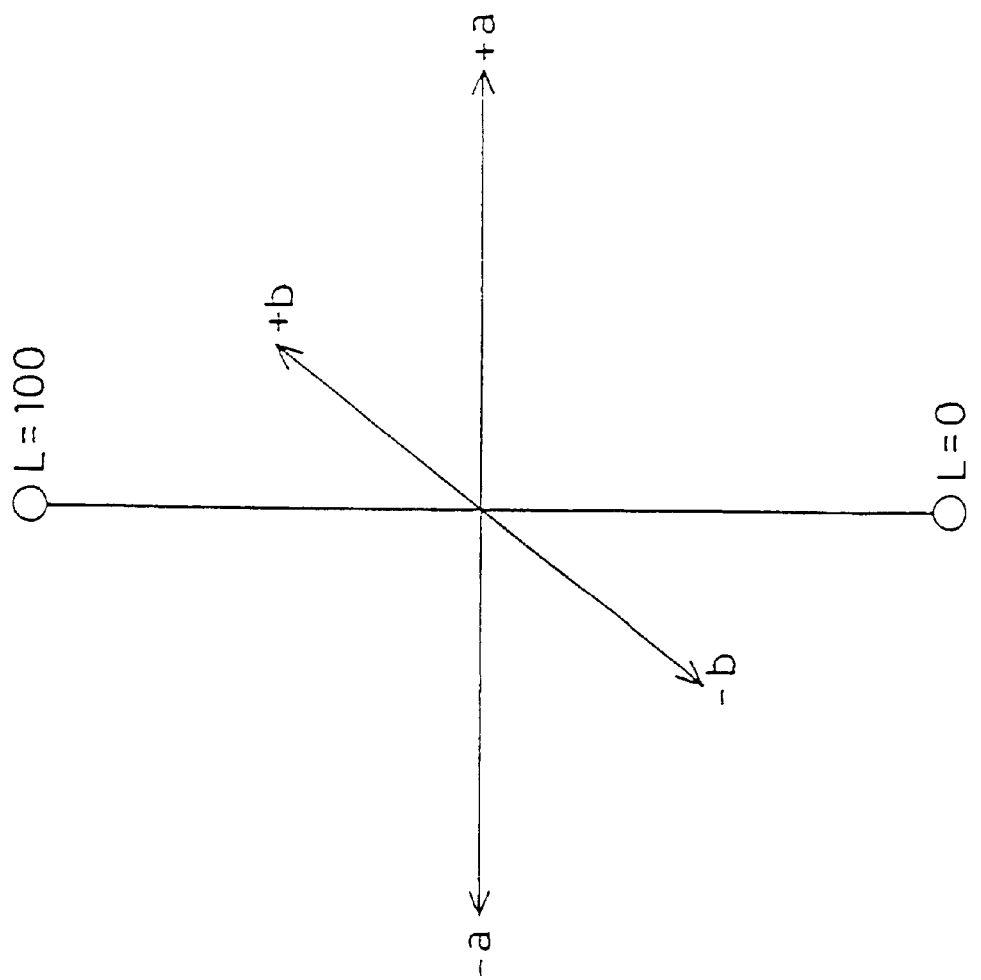
FIG. 1 is a representation of a coordinate system for colorometric measurement.

"Whiteness" as used herein generally refers to the absence of yellow. The whiteness of the microporous films herein may be measured using the Color Model of the ColorQUEST 45/0 instrumentation available from HunterLab, 11491 Sunset Hills Road, Reston, Va. 22090 USA. See also, *The Measurement of Appearance*, Hunter, Richard S., Hunter Associates Laboratories, 9529 Lee Highway, Fairfax, Va. 22030 USA. The Color Model describes the color of any material on the basis of three parameters: L, a, and b. The Color Model may be graphically represented by the coordinate system shown in FIG. 1. Referring to FIG. 1, in the coordinate system shown, "L" is a measure of the lightness of a sample, ranging from L=0 (blackness) to L=100 (whiteness). The quantities "a" and "b" are called opponent-type coordinates. They indicate the degree of redness (positive "a" values), greenness (negative "a" values); and the degree of yellowness (positive "b" values), blueness (negative "b" values). For neutral colors (e.g., white, gray, black), "a" and "b" should be about zero. The higher the values of "a" and "b" for a given sample, the more saturated or chromatic is the color of that sample.

The most important parameter for the films of the present invention is the "b" value, due to the lack of consumer acceptance of yellowish films. Using the ColorQUEST instrument under the conditions of the 10°/D65 international standard and a 100 reflecting angle, the "b" value for the films of the present invention is preferably between about 0.0 and about 0.5, more preferably as close to zero as possible.

In addition to the polyethylene and the $CaCO_3$, small amounts of other additives, such as antioxidants or lubricants, may also be added during the initial mixing stage of the film formation process. These other additives should preferably be added in the range of about 0.01 wt % to about 0.05 wt %.

"Microporosity" refers to the functional property of the film that permits an article such as a diaper to deliver improved skin health, because the microporous holes permit moisture vapor transmission between the inside of the diaper, i.e., the wearer's skin, and the outside of the diaper. Good moisture vapor transmission, or "breathability", also increases the wearer's comfort by providing a less stuffy feeling.

Moisture vapor transport rate ("MVTR") is a characteristic measure of breathability and "microclimate" inside the diaper. MVTR refers to the permissible moisture volume from one side of the film to the other side of the film per area unit (e.g., per square meter) and per time unit (e.g., per one day). High MVRR is desirable for good skincare because the air can be well ventilated between the inside and the outside of the diaper. However, if the MVTR is too high, the risk of odor, noticeable moisture leakage, or both is present. The control of MVTR is therefore important in applications involving microporous film technology.

The MVTR of a breathable film may be measured by the method set forth as follows. A known amount of calcium chloride ($CaCl_2$) is put into a flanged cup. A sample is placed on the top of the cup and held securely by a retaining ring and gasket. The assembly is then weighed and recorded as the initial weight. The assembly is placed in a constant temperature (40° C.) and humidity (75% relative humidity) chamber for 5 hours. The assembly is then removed from the chamber an allowed to equilibrate for at least 30 minutes at the temperature of the room where the balance is located. The assembly is then weighed and recorded as the final weight. The MVTR is calculated and expressed in $g/m^2/24$ hr. using the following formula:

$$MVTR = \frac{(\text{Final weight} - \text{initial weight}) \times 24.0}{\text{Area of sample in meters} \times 5.0 \text{ (time in chamber)}}$$

The films of the present invention preferably have an MVTR of at least about 3200 grams/$m^2$ per day, with about 3700 grams/$m^2$ per day being more preferable for diapers. Preferably, the MVTR is as high as possible with no leaks.

Figure 2:
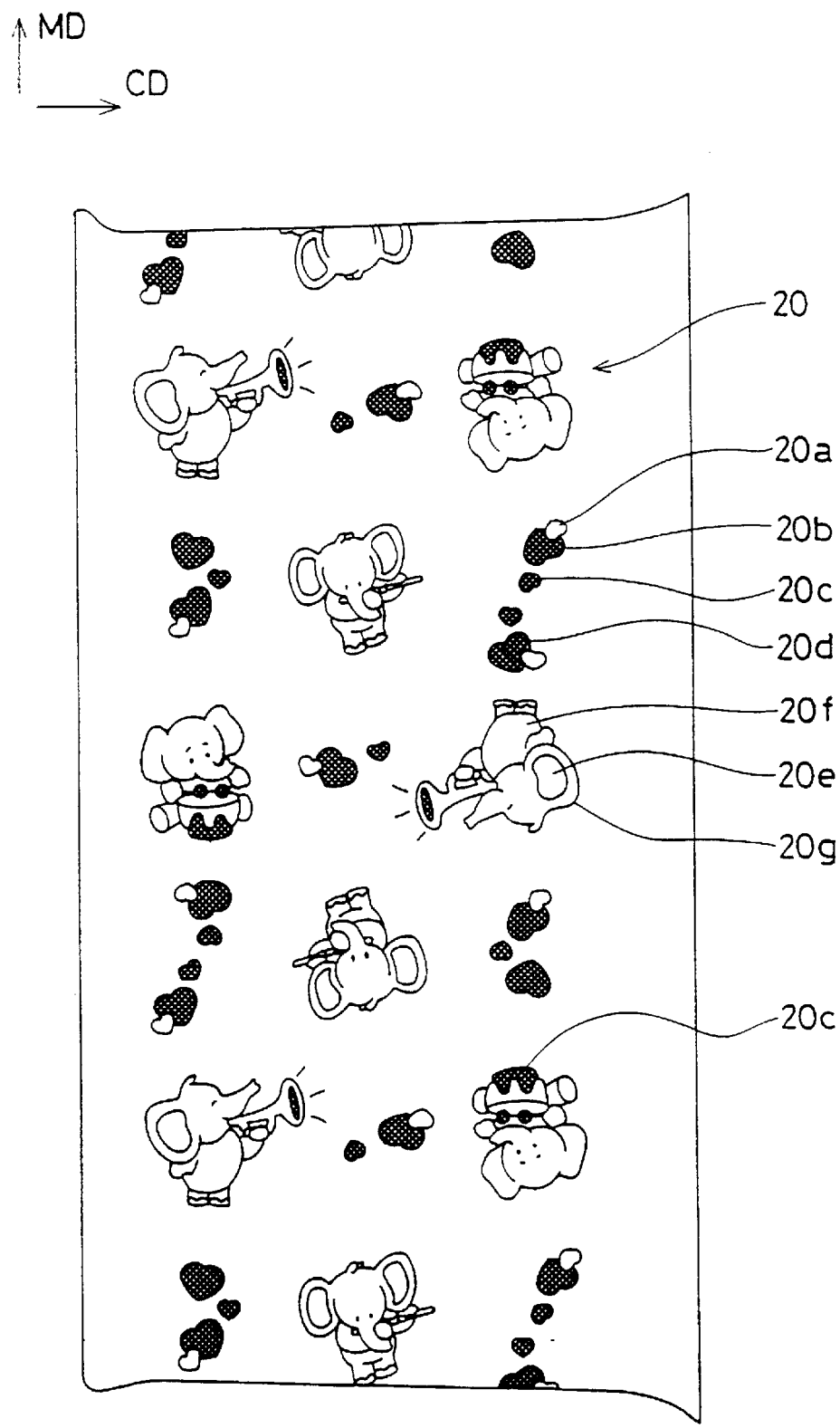
FIG. 2 is a partial plan view of a preferred embodiment of the backsheet film of the present invention printed with multicolored graphics.

An exemplary portion of a film of the present invention is shown in FIG. 2. A non-limiting example of a color and graphic pattern suitable for use herein is illustrated, where 20a represents the color yellow, 20b represents the color green, 20c represents the color royal blue, 20d represents the color red, 20e represents the color pink, 20f represents the color sky blue, and 20g represents the color dark blue (border color). It will be understood by those of skill in the art that the graphics 20 may be of any shape, design, color, or size, and that single or multiple designs and any style of character or theme may be used.

Printing techniques useful herein for applying the multi-colored graphics to the film include flexographic printing process and gravure printing process. The flexographic process generally comprises running the film between several printing and dummy cylinders and typically does not require that the film be subjected to a high degree of tension. The gravure process is a generally linear process in which more tension control is needed. For this reason, the flexographic printing process is preferred. Alternatively, other suitable printing techniques known to those of skill in the art may be used herein.

The films of the present invention exhibit good thermal stability as a result of the raw materials selection and the processing conditions, particularly the drawing and annealing steps. After the film has been formed and during the time in which it is subsequently stored, often in a warehouse where it is exposed to elevated temperatures after production, the film material tends to shrink. This shrinkage is a function of the time, temperature and humidity conditions of storage and transport, parameters that cannot readily be controlled. For example, during one week at 50° C., shrinkage levels of up to 5.0–10.0% have been observed for certain conventional films. Different levels of shrinkage can even vary within the same roll of film depending upon the time and temperature conditions during annealing, as well as the level of tension that was used to wind the particular roll. This thermal instability has typically made it difficult to incorporate high resolution multi-colored graphics into backsheet films for disposable absorbent articles, as the shrinkage distorts the appearance of the graphics and tend to render them unacceptable to consumers.

The thermal shrinkage rate of microporous films may be measured under the following conditions. Film samples are cut as 500 mm long in the machine direction and 150 mm wide in the cross direction. As used herein, "machine direction" means the direction of movement along a manufacturing line, and "cross direction" means the direction substantially perpendicular to the machine direction. The machine direction is represented by the arrow labeled MD in FIG. 2, and the cross direction is represented by the arrow labeled CD. Two straight lines are drawn as 250 mm in the machine direction and 100 mm in the cross direction. The film samples are placed into an oven controlled at 50° C. and 50% relative humidity for one week. The shrunken lengths of the lines are calculated as the thermal shrinkage rate, based upon the original lengths.

Under the test conditions described above, the films of the present invention typically experience less than about 4.0% shrinkage in the machine direction, more preferably as close to 0.0% as possible. In the cross direction, the films typically experience negligible shrinkage. Thus, the films of the present invention provide both the good surface characteristics of microporous polymer films that readily support multi-colored printed graphics while being susceptible to low levels of thermal shrinkage.

The films of the present invention also preferably have other desirable properties that are beneficial in connection with their use in absorbent articles. The following are non-limiting examples.

Basis weight refers to the weight of one square meter of planar web material and is important to consistent converting of the disposable absorbent articles during manufacture. Exemplary basis weights herein are between about 20 grams per square meter (gsm) and about 40 gsm for films useful as a diaper backsheet, with about 35 gsm being preferred for certain pull-on diaper executions.

The mechanical properties of the film, e.g., tensile strength and elongation, are also important for consistent converting of articles during manufacture and no tearing. Tensile strength refers to tensile strength at a percent strain or at peak, where strains in the range of about 1% to 5% represent strains in the elastic range of the material. The films herein preferably exhibit tensile strength of from about 1400 to about 2450 g/inch in the machine direction, and from about 350 to about 650 g/in in the cross direction. Elongation at peak is preferably from about 150 to about 300% in the machine direction, and from about 390 to about 620% in the cross direction.

Film caliper control is important to the winding of a roll of backsheet film and to its processability. The term "film caliper" refers to the thickness of the film. During the film making process, various localized levels of film shrinkage sometimes occur in the case of microporous films. A wide variation in film caliper may cause wrinkles or an uneven surface or both in a roll of film. During processing, caliper variations may cause film deformation, film breakage at the thinner areas, and line stoppage due to problems caused by tension control problems. Exemplary ranges for film calipers herein are in the range of about 0.03 mm to about 0.04 mm, with caliper variation of ±2.0%.

Thermal enthalpy ($\Delta H$) is another important characteristic in providing heat resistance to the polymer film, especially during processes such as hot-melt glue lamination that may be part of a diaper manufacturing line. A high enthalpy characteristic can provide a broad range for adhesive temperature adjustment because the film materials have strong heat-resistance. As enthalpy increases, however, the stiffness of the microporous film material also increases, leading to possible issues with comfort and other manufacturing processes that depend on heat response of the film. Without being bound by theory, it is believed that the link between added stiffness and rising enthalpy is due to rising forces between macromolecules.

Other film parameters that impact the printing process, the diaper manufacturing process, or both, include film width, length of the film roll, core diameter of the film roll, splices, and printing orientation.

An exemplary film suitable for use herein is manufactured by Mitsui Toatsu Chemicals, Inc., of Japan, under the designation "PG-P".

Preferably, the backsheet herein is comprised of at least a microporous polymer film printed with multicolored graphics, as described above. The backsheet preferably further comprises a layer of nonwoven material laminated to the microporous film layer, in which case there is provided a more cloth-like and garment-like feel than is typically obtained with a film backsheet only.

The nonwoven webs suitable for use in the backsheet laminates herein are preferably air pervious. Preferably, the nonwoven web covers all or substantially all of the outer-facing surface of the plastic film to provide the diaper with a cloth-like look and feel. Or, the nonwoven web may cover only discrete predetermined portions. The nonwoven web may comprise natural fibers (e.g. cotton or wood fibers), or may comprise fibers of polyethylene, polypropylene, polyester, polyethylene terephthalate, or may comprise blended fibers or multi-component fibers. Further, the nonwoven web may be carded, spunbonded, meltblown or air-through bonded or have any other characteristic or be manufactured in any manner known in the art. Preferably, the nonwoven web is comprised of sufficient amount of thermoplastic material to allow for thermal bonding of the material to other components of the diaper.

The cloth-like hand feeling of the backsheet is significantly increased with the use of the nonwoven web described herein. In general, the web of the present invention provides less rigidity and stiffness as well as less fuzz level than conventional nonwoven webs. This tends to bring about a comfortable, natural fabric feeling, improved skin health, and increased consumer acceptance. In conventional webs, stiff and fuzzy nonwovens can bring about undesirable skincare conditions for the baby, such as red marking caused by friction between the skin and the nonwoven, dirty broken microfibers (fuzz) from the nonwoven surface, and an overall dirty or greasy feeling during use. The nonwoven webs preferred for use herein have certain physical properties, described as follows.

Bending rigidity is a measure of the force required to bend a sample of a particular material. It is important to control the bending rigidity of the nonwoven web of the present invention in order to avoid red marking and provide adequate fit to the body of the wearer of the absorbent article. In addition, this property influences consumer preference as it relates to the feeling of stiffness or of flexibility that is perceived by the consumer.

Figure 3A:
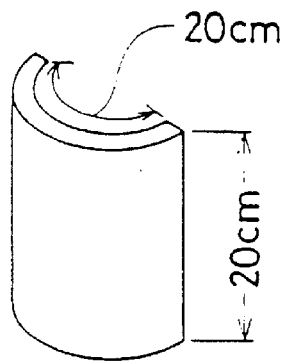
FIGS. 3A and 3B are schematic diagrams of the bending property measurement.
Figure 3B:
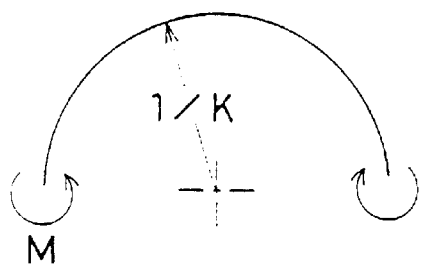
Figure 4:
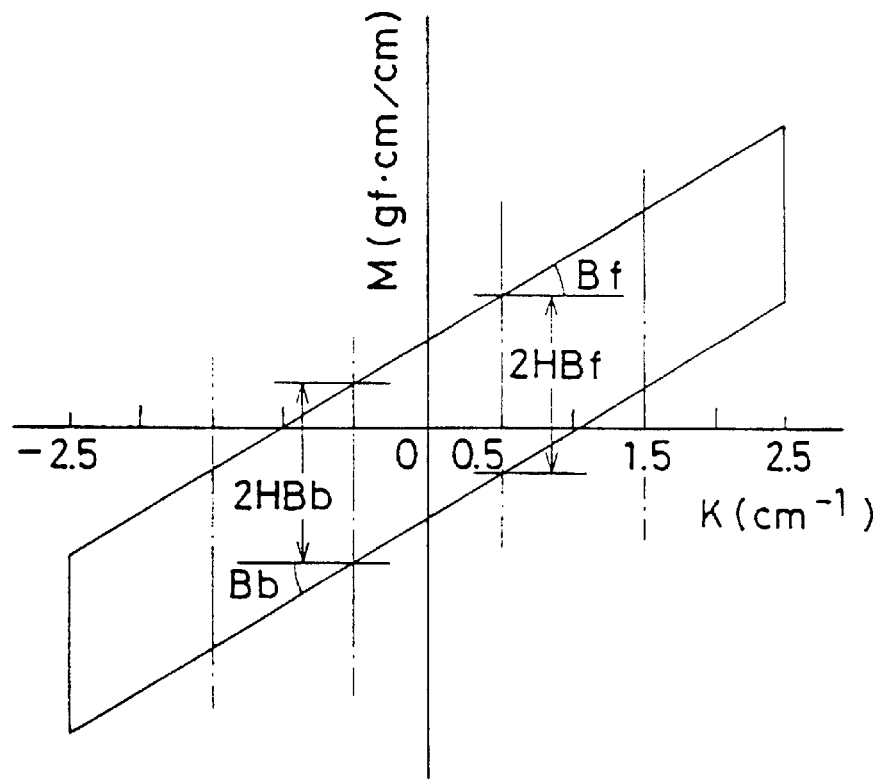
FIG. 4 is a graph showing the bending hysteresis curve.

The bending rigidity of a sample may be measured as follows. The deformation mode is a pure bending between the curvature K=−2.5 cm$^{-1}$ and 2.5 cm$^{-1}$. It is a measure of the force required to bend the sample. The standard sample size for this measurement is 20.0 cm in length and 20.0 cm in width (square). The sample is bent as shown in FIGS. 3A and 3B. The bending rate is 0.5 cm$^{-1}$/sec. As a result, the bending hysteresis curve as shown in FIG. 4 is obtained by the measurement. The horizontal axis shows the curvatures K cm$^{-1}$ and the vertical axis shows the moment M (gf·cm/cm). The value of B (bending rigidity per unit width of fabric) is calculated as follows:

$$B=(Bf+Bb)/2 \qquad (1)$$

where Bf and Bb are the slopes of the hysteresis curves between K=0.5 cm$^{-1}$ and 1.5 cm$^{-1}$ and K=−0.5 cm$^{-1}$ and −1.5 cm$^{-1}$ respectively. In preferred embodiments of the present invention, the nonwoven web has a bending rigidity B of about 35 to about 80 mg/cm$^2$/cm.

Shearing stiffness is another physical property that is also important to lessening of red marking and adequate fit to the body. In preferred embodiments of the present invention, the nonwoven web has a shearing stiffness of about 3.0 to about 4.0 g/cm deg. The shearing stiffness of a sample may be measured according to the following method.

Figure 5:
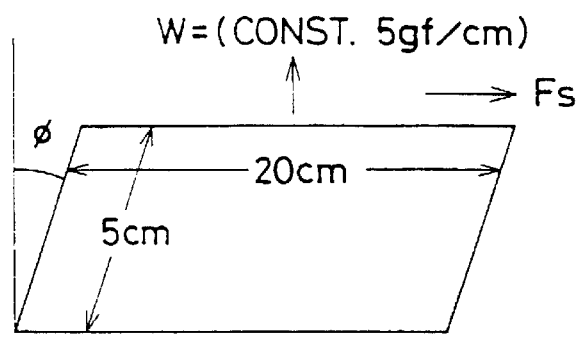
FIG. 5 is a plan view of the sample used for the shearing property measurement.
Figure 6:
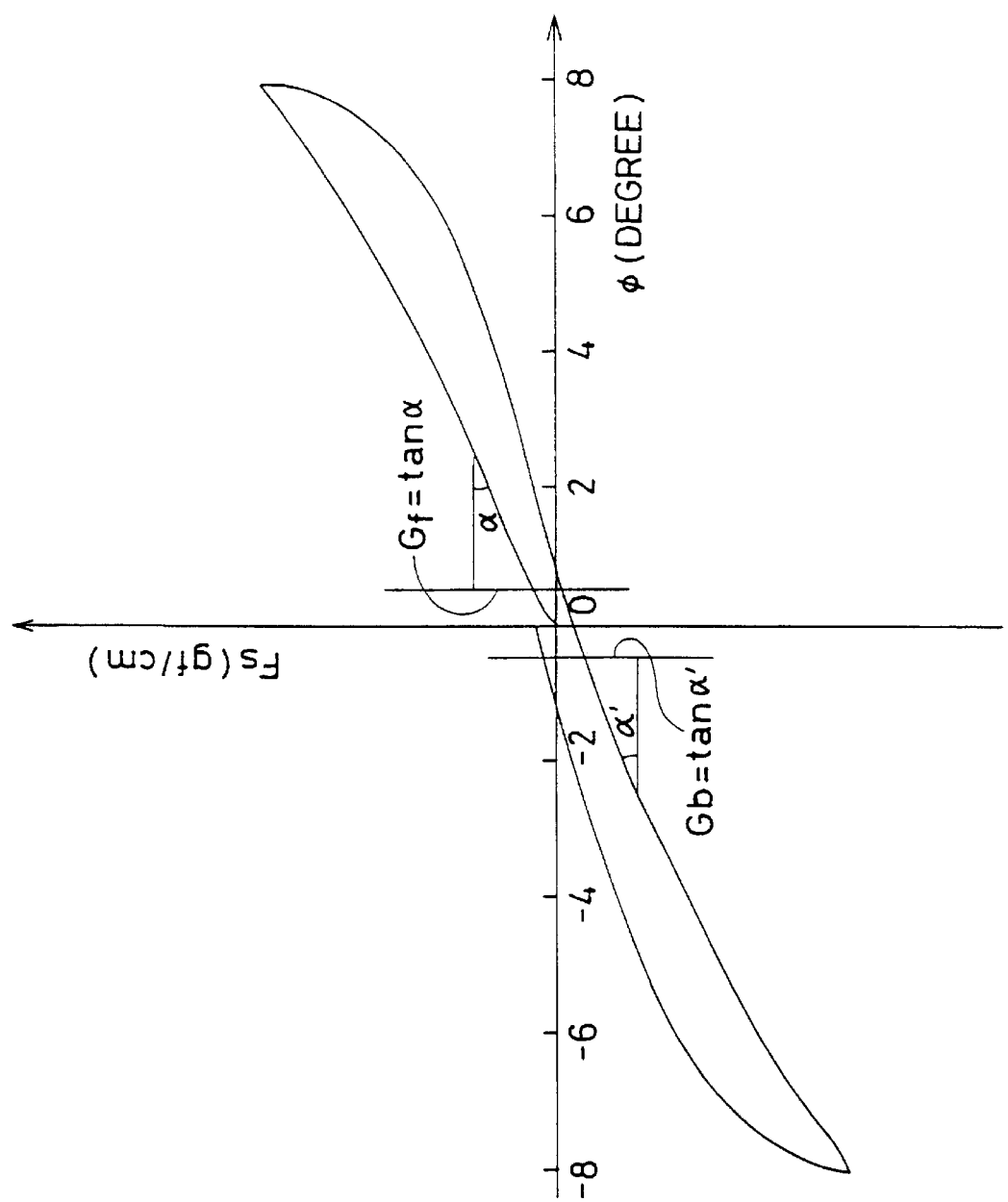
FIG. 6 is a graph showing the relationship between shearing angle and shear force.

The effective dimension of the sample for this measurement is 20.0 cm in width and 5.0 cm in length. A constant extension force, 5 gf/cm, is applied to the sample unidirectionally and then the shear force Fs is superposed in the sample plane along the transverse direction up to the shear angle ø=4°, as shown in FIG. 5. Then, the sample shear deformation is recovered by reducing the shear angle back to zero. The relationship between Fs and ø is obtained as shown in FIG. 6.

The value of G (shear stiffness) is calculated as follows:

$$G=(Gf+Gb)/2 \qquad (2)$$

where Gf and Gb are the average slopes between ø=0.5° and 5° and between ø=−0.5° and −5° respectively.

The coefficient of friction ("MIU") on the surface of the nonwoven is another important property that influences consumer preference, as it relates to good handfeel, and that affects skin health, as lowered values of MIU typically indicate lessening of red marking of the skin. Higher values of MIU typically correspond to higher values of friction. The MIU of a sample can be measured as described below.

Figures 7A, 7B:
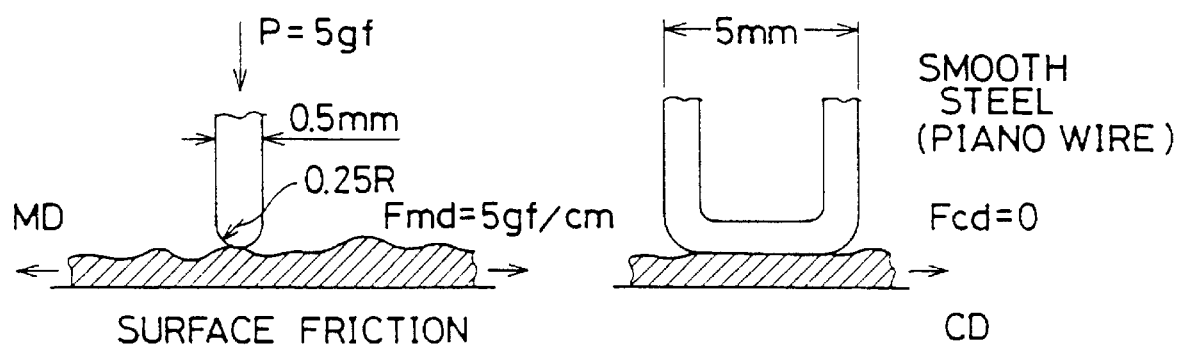
FIGS. 7A and 7B are schematic diagrams of the surface friction measurement.

To measure the surface friction of the sample, a pianowire of 0.5 mm in diameter and having a radius of 0.25 mm is prepared and bent as shown in FIGS. 7A and 7B, where FIG. 7A represents the machine direction (MD) view and FIG. 7B represents the cross direction (CD) view of the piano wire. A machine direction force Fmd of 5.0 gf (allowance, ±0.5 gf) of contact force is applied by a spring having a spring constant of 25±1 gf/mm. The natural frequency of the system should be more than 30 Hz when the contactor is out of contact. In the cross direction, no force is applied, as represented by Fcd=0 in FIG. 7B.

Figure 8:
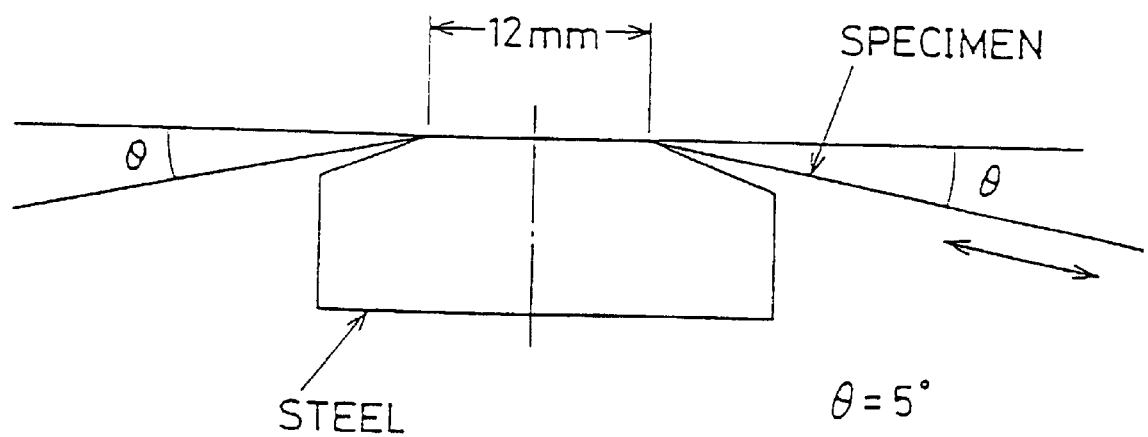
FIG. 8 shows the conditions of the steel plate used for the surface friction measurement.
Figure 9:
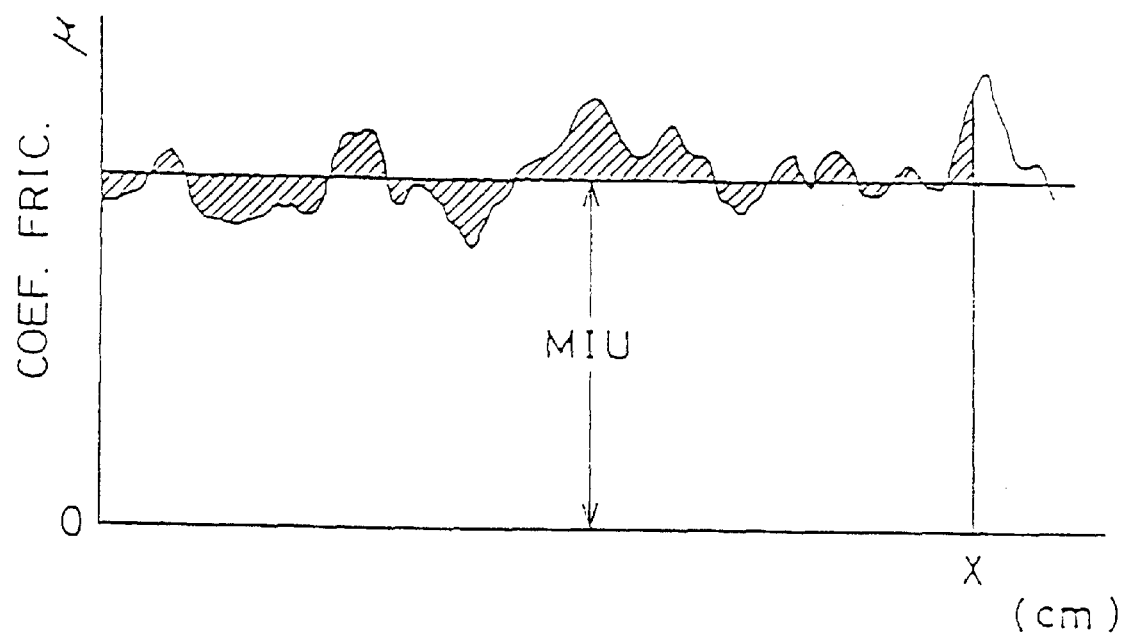
FIG. 9 shows the changes of the coefficient of friction along the surface of the sample.

In the surface friction measurement, the specimen is moved between a 2 cm interval at a constant velocity of 0.1 cm/sec on a smooth steel plate placed horizontally where the tension of the specimen is kept at 5.0 gf/cm (force per unit length) and the contactor is kept in its position. The dimension of the plate is shown in FIG. 8. The changes of the surface friction coefficient $\mu$ is mathematically obtained as shown in FIG. 9.

Consequently, the value of MIU is obtained from the following expression:

$$MIU = \frac{1}{X}\int_0^x \mu\, dx, \qquad (3)$$

where:

$\mu$; frictional force/compression force x; displacement of the contactor on the surface of sample X; distance for specimen movement, 2 cm is used for this measurement Preferably, the nonwoven webs of the present invention have MIU values of from about 0.2 to about 0.4.

A commercially available nonwoven web suitable for use herein is a spunbonded nonwoven web manufactured by the Fiberweb Company under the designation "DAPP S-tex". Alternatively, a carded nonwoven web may be suitable for use herein.

Figure 10:
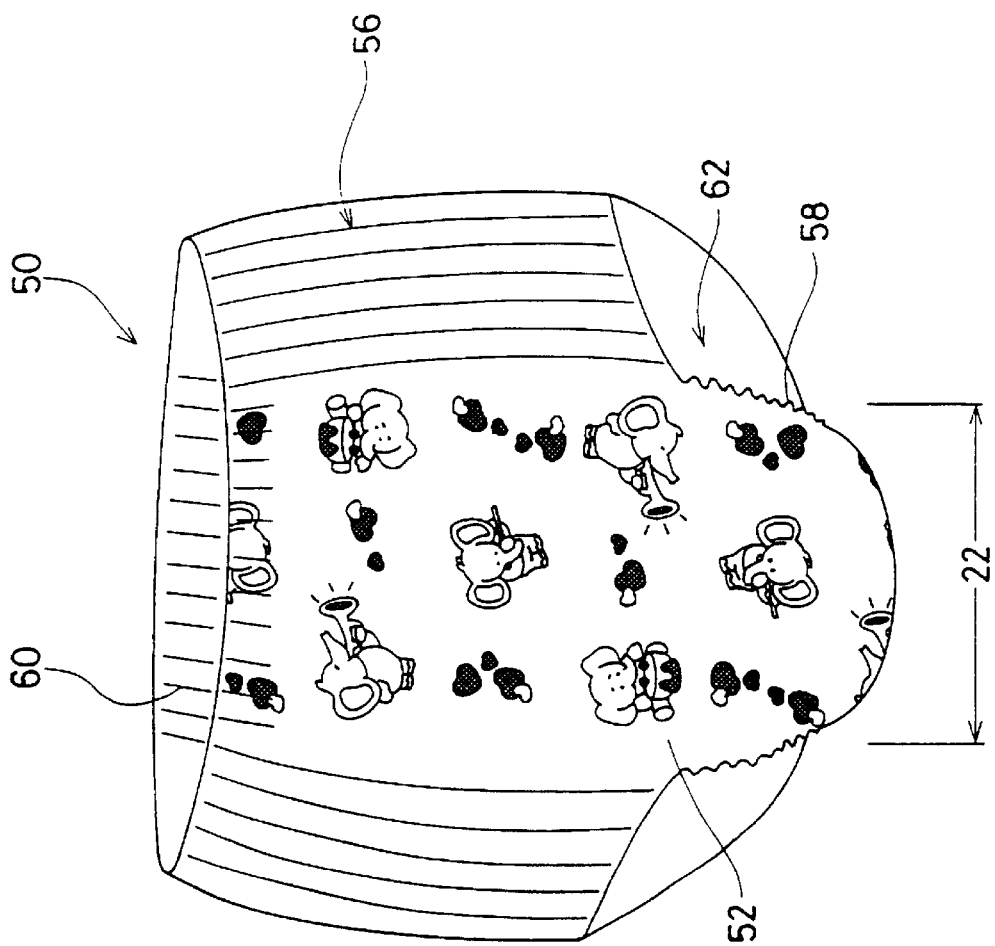
FIG. 10 is a front view of a preferred embodiment of a disposable absorbent article having a backsheet printed with multicolored graphics.

Referring to FIG. 10, a preferred embodiment of a disposable pull-on diaper 50, which is generally pulled onto the body of the wearer by inserting the legs into the leg openings 62 and pulling the article up over the waist, is shown. Generally, "pull-on diaper" refers to unitary pull-on garments having ear panels with edges that are seamed together to form the leg openings and a waist opening and that are worn by children who are able to walk and often who are toilet training. It should be understood that other pull-on garments such as training pants, pants for adult use, incontinent briefs, feminine briefs, feminine hygiene garments or panties, and like, are included herein.

It should also be understood that although the backsheet of the present invention is described herein primarily in the context of a pull-on type diaper, it will be understood this backsheet is equally useful for other types of disposable absorbent articles, e.g., "tape-type" diapers in which the rear portion of the diaper is manually attached to the front portion of the diaper on each side of the wearer, typically by means of adhesive or mechanical fasteners provided at the rear of the diaper and secured to a landing region on the front on the diaper.

Figure 11:
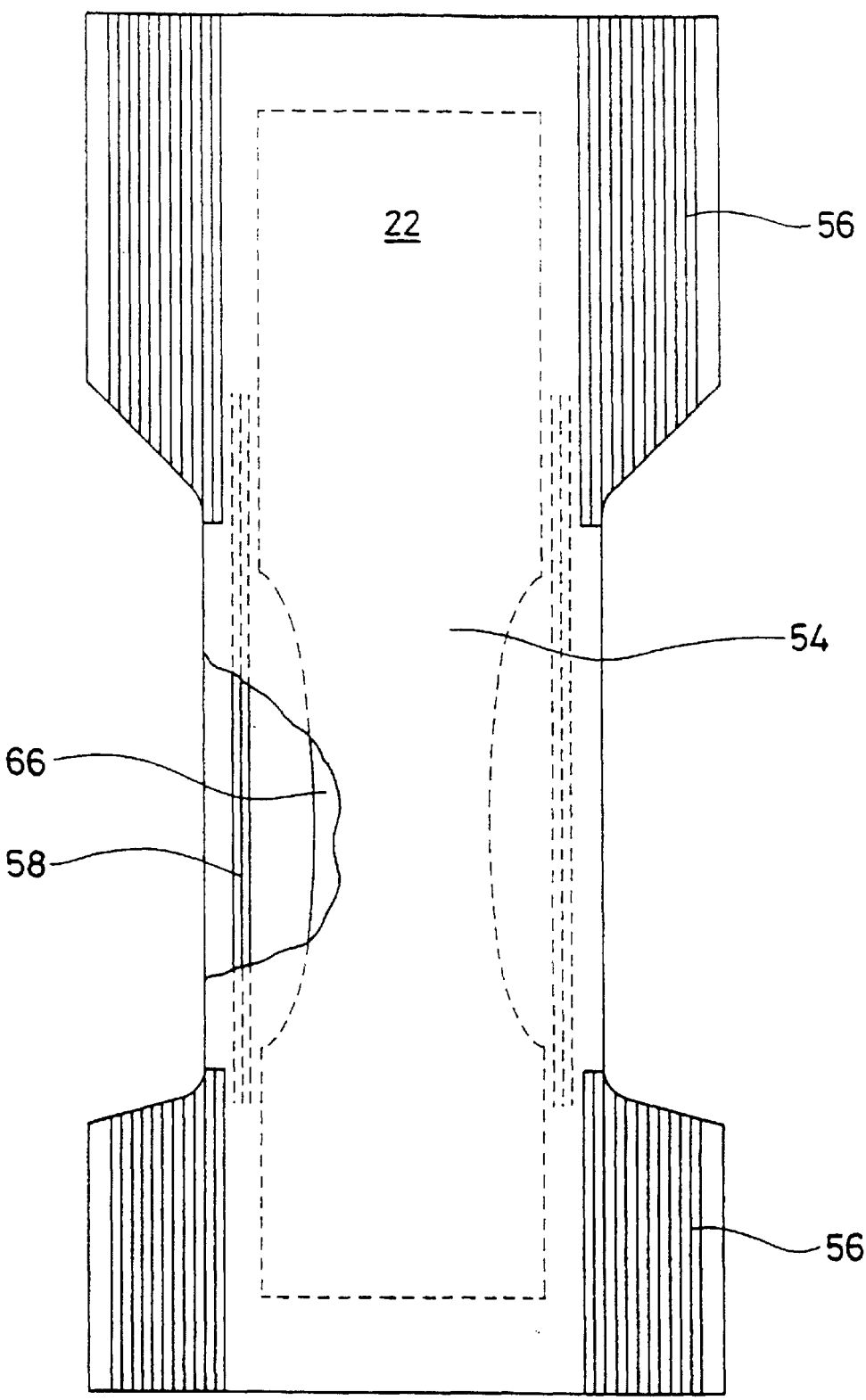
FIG. 11 is a simplified plan view of the pull-on garment of FIG. 10 in its flat uncontracted condition showing the inner (body facing) surface and having a portion cut away to reveal underlying structure.

Referring to FIGS. 10 and 11, a preferred embodiment of a disposable pull-on diaper 50 is shown. The diaper is generally comprised of a backsheet 52, a topsheet 54 and an absorbent layer or core 66 located between the backsheet 52 and the topsheet 54. The topsheet 54 is located to be placed facing the body or nearest the body when the diaper is worn and is generally provided with a liquid permeable region so that body exudates can flow through the topsheet 54 to the absorbent layer 66. The backsheet 52, which is placed away from the body during wear, is typically liquid impermeable so that outer clothing or other articles are not wetted by the body exudates.

Preferably, the backsheet 52 is comprised of at least a microporous polymer film printed with multicolored graphics, as described herein. The backsheet 52 preferably further comprises a layer of nonwoven material laminated to the microporous film layer, as described above, in which case a more cloth-like and garment-like feel than is typically obtained with a film backsheet only is provided. In preferred embodiments the plastic film exists only in the containment area 22 and does not exist in the ear panel areas 56 while the nonwoven web exists in both of the containment assembly area 22 and the ear panel areas 56. The nonwoven web thus preferably covers all of the outer facing surface of the plastic film.

The topsheet 54 and the backsheet 52 have length and width dimensions generally larger than those of the absorbent layer 66. Thus, the topsheet 54 and the backsheet 52 extend beyond the edges of the absorbent layer to form the periphery of the diaper. While the topsheet 54, the backsheet 52 and the absorbent layer 66 may be assembled in a variety of configurations, an exemplary configuration is described in Buell U.S. Pat. No. 3,860,003, "Contractible Side Portions for Disposable Diaper", and in Buell U.S. Pat. No. 5,151,092.

The absorbent layer 66 may be any absorbent member which is generally compressible, conformable, non-irritating to the wearer's skin, and capable of absorbing and retaining liquids such as urine and other exudates. The absorbent layer may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles.

The configuration and construction of the absorbent core 66 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core may also be varied to accommodate wearers ranging from infants through adults.

The topsheet 54 is preferably positioned adjacent the inner surface of the absorbent core 66 and is preferably joined thereto and to the backsheet 52 by attachment means (not shown) such as those well known in the art.

The topsheet 54 is preferably compliant, soft feeling, and non-irritating to the wearer's skin. Further, the topsheet 54 is preferably liquid pervious permitting liquids (e.g., urine) to readily penetrate through its thickness. The topsheet 54 is preferably made of a hydrophobic material to isolate the wearer's skin from liquids which have passed through the topsheet 54 and are contained in the absorbent core 66 (i.e. to prevent rewet). If the topsheet 54 is made of a hydrophobic material, at least the upper surface of the topsheet 54 is treated to be hydrophilic, e.g. by treating it with a surfactant, so that liquids will transfer through the topsheet more rapidly. This diminishes the likelihood that body exudates will flow off the topsheet 54 rather than being drawn through the topsheet 54 and being absorbed by the absorbent core 66.

An alternative preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer.

In addition, skin care-type topsheets that are provided with lotion or other skin health agents thereon for the purpose of reducing skin irritation and chafing are a desirable feature herein.

The backsheet 52 is preferably positioned adjacent the outer surface of the absorbent core 66 and is preferably joined thereto by any suitable attachment means known in the art. For example, the backsheet 52 may be secured to the absorbent core 28 by a uniform continuous layer of adhesive, a patterned layer of adhesive, or an array of separate lines, spirals, or spots of adhesive. Alternatively, the attachment means may comprise heat bonds, pressure bonds, ultrasonic bonds, dynamic mechanical bonds, or any other suitable attachment means or combinations of these attachment means as are known in the art.

Embodiments of the present invention are also contemplated wherein the absorbent core 66 is not joined to the backsheet 52, and/or the topsheet 54 in order to provide greater extensibility in the front waist region 46 and the rear waist region 44. Alternative embodiments are contemplated wherein an additional member, such as a liquid impervious barrier material(s) (not shown), is positioned between the outer surface of the absorbent core 66 and the backsheet 52. Any such barrier member may or may not be joined to the absorbent core 66. Further, the backsheet 52 may or may not be joined to any barrier material(s) that are positioned between the backsheet 52 and the absorbent core 66.

The diaper further comprises at least one pair of extensible ear panels 56 each extending laterally outwardly from the sides of the containment assembly 22. The ear panels 56 are joined, e.g., by seams, to form the two leg openings and the waist opening, as seen in FIG. 10. The ear panels 56 are preferably elastically extensible in at least the lateral direction are provided to ensure more comfortable and contouring fit by initially conformably fitting the pull-on diaper 50 to the wearer and sustaining this fit throughout the time of wear well past when it has been loaded with exudates, since the ear panels permit the sides of the diaper to expand and contract.

An elasticized waistband 60 (shown in FIG. 10) may also be provided in order to provide improved fit and containment, as disclosed in e.g., U.S. Pat. No. 4,515,595, entitled "Disposable Diapers with Elastically Contractible Waistband issued to Kevit et al. on May 7, 1985.

Elasticized leg cuffs 58 may further be provided. These leg cuffs may comprise any of several different embodiments for reducing the leakage of body exudates in the leg regions. The leg cuffs may also be referred to as leg bands, side flaps, barrier cuffs or elastic cuffs. Non-limiting examples leg cuff configurations suitable for use here include those described in U.S. Pat. No. 4,695,278 entitled "Absorbent Article Having Dual Cuffs" issued to Lawson on Sep. 22, 1987, and U.S. Pat. No. 4,795,454 entitled "Absorbent Article Having Leakage Resistant Dual Cuffs", issued to Dragoo on Jan. 3, 1989.

As will be understood by those of skill in the art, many other features for disposable absorbent articles are within the scope of the present invention.

The aspects and embodiments of the present invention set forth herein have many advantages, including consumer appeal due to bright white appearance, aesthetic multi-colored graphics, and good cloth-like feeling and improved skin health.

It is understood that the examples and embodiments described herein are for illustrative purposes only and that various modifications or changes in light thereof will be suggested to one skilled in the art without departing from the scope of the present invention.

What is claimed is:

1. A disposable absorbent article comprising a topsheet, a backsheet and an absorbent layer between the topsheet and the backsheet, wherein the backsheet is comprised of a microporous polymer film printed with multicolored graphics and a nonwoven material laminated to the film, wherein the film has a "b" value between about 0.0 and about 0.5 and exhibits less than about 4.0% thermal shrinkage at about 50° C. and about 50% relative humidity for one week.

2. The article of claim 1 wherein the nonwoven material has a bending rigidity from about 35 to about 80 mg/cm$^2$/cm.

3. The article of claim 1 wherein the nonwoven material has a coefficient of friction between about 0.2 and 0.4.

4. The article of claim 1 wherein the nonwoven material has a shearing stiffness between about 3.0 to about 4.0 g/cm deg.

5. The article of claim 1 wherein the film has a tensile strength from about 1400 to about 2450 g/in in the machine direction.

6. The article of claim 1 wherein the film has a tensile strength from about 350 to about 650 g/in in the cross direction.

7. The article of claim 1 wherein the film has a moisture vapor transmission rate of at least about 3200 grams/m$^2$ per 24 hours.

* * * * *

UNITED STATES PATENT AND TRADEMARK OFFICE
CERTIFICATE OF CORRECTION

PATENT NO. : 6,569,136 B1
DATED : May 27, 2003
INVENTOR(S) : Jie Tao et al.

It is certified that error appears in the above-identified patent and that said Letters Patent is hereby corrected as shown below:

<u>Column 4,</u>
Line 12, delete "MVRR" and insert -- MVTR --.

Signed and Sealed this

Thirty-first Day of January, 2006

JON W. DUDAS
*Director of the United States Patent and Trademark Office*